United States Patent [19]
Bohn et al.

[11] Patent Number: 6,007,798
[45] Date of Patent: Dec. 28, 1999

[54] PREPARATIONS STIMULATING NAIL GROWTH

[75] Inventors: Manfred Bohn, Hofheim; Karl Theodor Kraemer, Langen; Horst Ulbricht, Biebergemünd, all of Germany

[73] Assignee: Hoechst Aktiengesellschaft, Frankfurt am Main, Germany

[21] Appl. No.: 08/930,562

[22] PCT Filed: Jan. 23, 1997

[86] PCT No.: PCT/EP97/00311

§ 371 Date: Feb. 11, 1998

§ 102(e) Date: Feb. 11, 1998

[87] PCT Pub. No.: WO97/28790

PCT Pub. Date: Aug. 14, 1997

[30] Foreign Application Priority Data

Feb. 6, 1996 [DE] Germany ............................ 196 04 190

[51] Int. Cl.$^6$ ............................ A61K 7/04; A01N 25/00
[52] U.S. Cl. ............................................ 424/61; 424/405
[58] Field of Search ........................................ 424/61, 401

[56] References Cited

U.S. PATENT DOCUMENTS 4,927,626  5/1990  DeVillez et al. .......................... 424/61
4,957,730  9/1990  Bohn et al. ............................... 424/61

*Primary Examiner*—Thurman K. Page
*Assistant Examiner*—Sharon Howard
*Attorney, Agent, or Firm*—Finnegan, Henderson, Farabow, Garrett & Dunner, L.L.P.

[57] ABSTRACT

A nail varnish comprising a compound having a vasodilating action and a water-insoluble film-forming agent is suitable for treatment of growth disturbances of the nail.

20 Claims, No Drawings

PREPARATIONS STIMULATING NAIL GROWTH

The invention relates to a nail varnish comprising a nail growth-promoting compound and a water-insoluble film-forming agent, to processes for its preparation and to the use thereof for the treatment of growth disturbances of the nail.

The nail plate which seals and protects the nail is a horny, hard appendage of the skin of the fingertip or tip of the toe which grows out of a pocket-like invagination of the epidermis on the finger or the back of the toe.

The formation of the nail material for the nail plate is effected primarily in the nail matrix, a specialized tissue which occupies the lower portion of the nail pocket from its proximal end up to the lunula. The nail matrix region is adjacent distally to the nail bed, with which the nail plate, which is structured in the form of a longitudinal strip on its under-surface, firmly adheres up to the hyponychium. The hyponychium is the dorsal region of the epidermis lying between the nail bed and finger pad.

The surface of the nail plate is smooth, and its color is a delicate pink as a result of corial capillaries showing through. Only an area 1–5 mm in size in the shape of a half-moon—the lunula—present at the proximal end looks whitish.

The growth rate of the nail plate, i.e. its increase in length beyond the free edge, depends on the extent of regeneration of nail cells in the nail matrix. The cell material formed there differentiates into plate-like horny structures which are passively pushed in the distal direction. The nail grows continuously throughout the entire life of the organism. The growth rate decreases with old age. The average weekly increase in length of the fingernails is 0.5 to 1.2 mm, and, in addition to age and sex, circulation, diet and physiological stress can have an influence on this value. The nails on the working hand are said to grow faster. Toenails grow significantly more slowly than fingernails, especially in older persons.

In the case of a normal nail growth rate of someone about 35 years old, the time needed for a new fingernail to grow out is about 6 months, and a toenail is regenerated in about 12 months.

In addition to constitutional factors which lead to an absence of nail growth, numerous local or general disease processes and also effects due to poisons, medicaments, chemicals and traumas can adversely influence the growth and appearance of the nail.

Nail growth plays a quite decisive role in the treatment and the required duration of treatment of onychomycoses; onychomycoses are understood as meaning infections of the nail bed which are caused by fungi and, as the duration of the disease increases, can extend over the entire nail, including the visible portion of the nail plate.

In the case of distal subungual onychomycoses, the clinical type to be observed most frequently, the pathogens attack the nail organ by first gaining access to the hyponychial horny layer. As the infection progresses further, the underside of the nail plate is also attacked. In later stages, discolorations and restructuring occur in the nail plate, as a result of which the appearance of the nail changes completely. Keratophilic fungi such as *Trichophyton rubrum* or *T. mentagrophytes* change the nail plate in a quite characteristic manner. They lead to a visible discoloration, which is accompanied by destruction of the lamellar structure of the nail plate in the progressing stage and finally leads to complete destruction of the protective shield. As the infection progresses, the subungual tissue debris of the hyponychium and of the nail bed is an ideal breeding ground for further microorganisms, which in turn contribute toward additional change in the chemical and physical properties of the underside of the nail plate. Finally, the nail plate initially becomes detached from the nail bed, which is associated with great pain for the patient when moved. Those affected can thus lose the entire nail plate due to the action of the fungi, so that only the hypokeratotic nail bed remains, which is thus rendered unprotected against external influences. Directed movements are now hardly possible because of the absence of the nail plate, which functions as an abutment.

The rate of spreading of the infection differs from case to case. It depends on the one hand on the growth rate of the penetrating microorganisms from the free end of the nail in the direction of the nail matrix, and on the other hand on the growth rate of the nail from the nail matrix in the direction of the free end of the nail.

Only a healthy nail is protected against penetration of microorganisms from the free end of the nail on the basis of its growth rate. However, if nail growth proceeds more slowly because of age or illness, the microorganisms can spread unimpeded if untreated.

One known treatment of onychomycoses is currently topical treatment of the diseased nails with varnish formulations having an antimycotic action, sometimes in combination with antimycotics having a systemic action. One disadvantage of this treatment method is that treatment must be administered for a relatively long time until the diseased nail has healed clinically, i.e. until the nail areas affected have grown out and a new nail has regrown cleanly. This means that the treatment, which usually takes several months, is often not kept up by the patient, and that as a result therapeutic success is absent. The topical/systemic combination treatment frequently used also represents a considerable cost factor because of the price situation of systemic antimycotics.

It has now been found that the growth of nails can be accelerated if the formulation according to the invention is applied to the nails, in particular to the diseased nails. The formulations are not only suitable as an additional supporting measure for accelerating growth during specific treatment of onychomycoses, but can also be employed for treatment of nail growth disturbances of varying origin.

The invention therefore relates to a nail varnish comprising a water-insoluble film-forming agent and at least one compound having a vasodilating action.

Compounds which have a vasodilating action are, for example,

1. Compounds of the Formula I

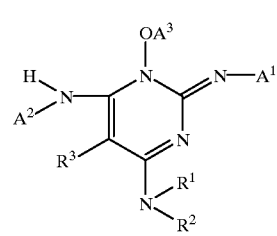

in which $R^1$ and $R^2$ independently of one another are
1) a hydrogen atom,
2) $(C_1-C_8)$-alkyl,
3) $(C_2-C_8)$-alkenyl,
4) phenyl-$(C_1-C_8)$-alkyl,
5) naphthyl-$(C_1-C_4)$-alkyl or 6) $(C_3-C_8)$-cycloalkyl, or
7) $R^1$ and $R^2$, together with the N atom, form a heterocyclic radical from the group consisting of
   7.1 aziridinyl,
   7.2 azetinyl,
   7.3 pyrrolidinyl,
   7.4 piperidinyl,
   7.5 hexahydroazepinyl,
   7.6 heptamethylimino,
   7.7 octamethylimino,
   7.8 morpholinyl or
   7.9 4-$(C_1-C_4)$-alkyl-piperazinyl, or
8) a radical from 7), in which the carbon atoms of the heterocyclic radicals are substituted by 1 to 3 $(C_1-C_4)$-alkyl radicals, $R^3$ is
1) a hydrogen atom,
2) $(C_1-C_8)$-alkyl,
3) $(C_2-C_8)$-alkenyl,
4) phenyl-$(C_1-C_8)$-alkyl,
5) naphthyl-$(C_1-C_8)$-alkyl,
6) benzyl,
7) phenyl,
8) naphthyl,
9) $(C_3-C_8)$-cycloalkyl or
10) $(C_1-C_6)$-alkyl, which is mono- or polysubstituted by halogen, and $A^1, A^2$ and $A^3$ independently of one another are a hydrogen atom or acetyl.

A preferred compound of the formula I is that in which
$R^1$ and $R^2$, together with the N atom, form the heterocyclic radical piperidinyl,
$R^3$ is a hydrogen atom and
$A^1, A^2$ and $A^3$ independently of one another are a hydrogen atom or acetyl.

A particularly preferred compound of the formula I is that in which
$R^1$ and $R^2$, together with the N atom, form the heterocyclic radical piperidinyl and
$R^3, A^1, A^2$ and $A^3$ are hydrogen atoms.

2. Compounds such as dihydralazine, diisopropylamine or diazoxide.
3. Calcium antagonists, such as nifedipine, nicardipine, verapamil, diltiazem, nisoldipine, nitrendipine, nivaldipine, isradipine, felodipine, nimodipine, gallopamil, fendiline, flunarizine, amlodipine, diperdipine, fluspirilene, primozide, fantofarone, nicergoline or clycandelate.
4. Angiotensin converting enzyme inhibitors, such as quinapril, lisinopril, benzazepril, captopril, ramipril, fosinopril, cifazapril or trandolapril.
5. Methylxanthine compounds, such as pentoxifylline, propentofylline or torbafylline.
6. Hair growth-promoting compounds such as inner salts of 2,4-diamino-6-alkoxy-3-sulfoxypyrimidine hydroxide having 1 to 6 carbon atoms in the alkoxy radical as described in EP 0 427 625 or the inner salt of 2,4-diamino-6-butoxy-3-sulfoxypyrimidine hydroxide;
pyridine 1-oxide derivatives as described in WO 92 21317 or 2,6-diamino-4-piperidinopyridine; 2,6-diamino-1,3,5-triazine derivatives as described in WO 91 19701 or 2,6-diamino-4-butoxy-1,3,5-triazine 1-oxide.

The compound of the formula I is prepared as described in U.S. Pat. No. 3,461,461.

With the nail varnish according to the invention as an additional supporting measure for accelerating growth, the treatment time of specific treatment of onychomycoses can be shortened considerably, which, in addition to optimizing treatment costs, contributes towards a considerable improvement in patient compliance. This is an extremely important finding in respect of the poor experiences of treatment to date as a result of a lack of compliance by the patient, for whom the healing success does not become visible quickly enough.

The water-insoluble varnish film present after the varnish formulation has dried also has the advantage over hydrophilic systems that it is not removed from the nail surface during washing, bathing or showering, i.e. does not have to be reapplied again after these actions. It also prevents the active compound which has already penetrated into the nail from being dissolved out again during manipulation with water.

The treatment of distal subungual onychomycoses in the early stage is also possible with the nail varnish according to the invention without an additional specific antimycotic treatment.

The use of the nail varnish according to the invention is not limited exclusively to treatment or to an additional measure during treatment of onychomycoses. The nail varnish according to the invention can also be employed for treatment of nail growth disturbances of various other origins.

The content of active compound in the nail varnish according to the invention depends on the structure of each active compound and therefore on its release from the varnish film and its penetration properties in the nail.

The nail varnish according to the invention, i.e. the use form comprising a solvent, in general comprises the active compound in an amount of 0.1 to 10, preferably 2 to 5% by weight.

In addition to the active compound dissolved in a solvent or solvent mixture, the nail varnishes according to the invention also comprise, as necessary constituents, one or more film-forming agents which form a water-insoluble film on the nail after the formulation has dried.

Suitable film-forming agents are, for example, substances based on cellulose nitrate or physiologically acceptable polymers such as are customary in cosmetics, preferably as a mixture with cellulose nitrate. Examples which may be mentioned are polyvinyl acetate and partly hydrolyzed polyvinyl acetate, copolymers of vinyl acetate on the one hand and acrylic acid or crotonic acid or a maleic acid monoalkyl ester on the other hand, ternary copolymers of vinyl acetate on the one hand and crotonic acid and vinyl neodecanoate, or crotonic acid and vinyl propionate on the other hand, copolymers of methyl vinyl ether and a maleic acid monoalkyl ester, in particular maleic acid monobutyl ester, copolymers of fatty acid vinyl esters and acrylic acid or methacrylic acid, copolymers of N-vinylpyrrolidone, methacrylic acid and a methacrylic acid alkyl ester, copolymers of acrylic acid and methacrylic acid or an acrylic acid alkyl ester or methacrylic acid alkyl ester, in particular with a content of quaternary ammonium groups, or polymers, copolymers or mixtures comprising ethyl acrylate, methyl methacrylate or trimethylammonioethyl methacrylate chloride, or polyvinylacetals and polyvinylbutyrals, alkyl-substituted poly-N-vinylpyrrolidones, alkyl esters of copolymers of olefins and maleic anhydride, and reaction products of colophony with acrylic acid. In the esters, the alkyl radicals are usually short-chain and in most cases have not more than four carbon atoms.

Possible physiologically acceptable solvents are substances such as hydrocarbons, halogenated hydrocarbons, alcohols, ethers, ketones and esters which are customary in cosmetics, in particular acetic acid esters of monohydric alcohols, such as ethyl and butyl acetate, if appropriate mixed with aromatic hydrocarbons, such as toluene, and/or alcohols, such as ethanol or isopropanol.

The combination of the solvents is known to be of decisive importance for the drying time, brushability and other important properties of the varnish or of the varnish film. The solvent system preferably comprises an optimum mixture of low-boiling constituents (=solvents having a boiling point of 100° C.) and medium-boiling constituents (=solvents having a boiling point up to 150° C.), if appropriate with a small content of high-boiling constituents (=solvents having a boiling point up to 200° C.).

The nail varnishes according to the invention can furthermore be given the additives customary in cosmetics, such as plasticizers based on phthalate, glyceryl triacetate or camphor, dyestuffs or colored pigments; pearlescent agents, agents which delay sedimentation, sulfonamide resins, silicates, odoriferous substances, wetting agents, such as sodium dioctylsulfosuccinate, lanolin derivatives, light protection agents, such as 2-hydroxy-4-methoxybenzophenone, antibacterially active substances and substances having a keratolytic and/or keratoplastic action, such as ammonium sulfite, esters and salts of thioglycolic acid, urea, allantoin, enzymes and salicylic acid.

Colored or pigmented nail varnishes have the advantage, for example, that the formulation according to the invention can be adapted to suit the esthetic perception of the patient, and the currently existing changes in the nail are not immediately visible to other people.

The process according to the invention for the preparation of the nail varnish comprises mixing the water-insoluble film-forming agent, in dissolved form, with the active compound or active compounds and, if necessary, further processing the formulation.

The invention furthermore relates to a nail varnish comprising
1. a water-insoluble film-forming agent,
2. a vasodilating compound and
3. an antimycotic having a topical action.

Antimycotics having a topical action are hydroxypyridones, such as ciclopirox, piroctone or rilopirox, morpholine derivatives, such as amorofine, azoles, such as bifonazole, clotrimazole, econazole, miconazole, oxiconazole, croconazole, fenticonazole, tioconazole, ketoconazole or isoconazole or allyl compounds, such as terbinafin or naftifin, as well as griseofulvin, tolciclate, tolnaftate and butenafin.

Suitable hydroxypyridones which may further be mentioned are, for example: 1-hydroxy-4-methyl-6-n-hexyl-, -6-iso-hexyl-, -6-n-heptyl- or -6-iso-heptyl-2-pyridone, 1-hydroxy-4-methyl-6-octyl- or -6-iso-octyl-2-pyridone, and in particular 1-hydroxy-4-methyl-6-(2,4,4-trimethylpentyl)-2-pyridone, 1-hydroxy4-methyl-6-cyclohexyl-2-pyridone, 1-hydroxy4-methyl-6-cyclohexylmethyl- or -6-cyclohexylethyl-2-pyridone, in which the cyclohexyl radical can in each case also carry a methyl radical, 1-hydroxy- 4-methyl-6-(2-bicyclo[2.2.1] heptyl)-2-pyridone, 1-hydroxy-3,4-dimethyl-6-benzyl- or -6-dimethylbenzyl-2-pyridone and 1-hydroxy-4-methyl-6-(β-phenylethyl)-2-pyridone.

The content of water-insoluble film-forming agent, vasodilating compound, solvents and further additives corresponds to that of the abovementioned nail varnish without an antimycotic.

The content of antimycotics having a topical action in the nail varnish according to the invention depends on the structure of the particular antimycotic and on the release thereof from the varnish film, its penetration properties in the nail and its antimicrobial properties.

The nail varnish according to the invention, the use form comprising the solvent, in general comprises the antimycotic having a topical action in an amount of 0.5 to 20, preferably 2 to 15% by weight (wt. %). The minimum content in medicinal nail varnishes for treatment of mycoses is 4 wt. %; the nail varnishes used for prophylaxis comprise less than 4 and at least 1 wt. % of the antimycotic. In each case based on the amount of non-volatile constituents, i.e. the sum of the film-forming agents, vasodilating compound, any pigments present, plasticizer and other non-volatile additives and of the antimycotic having a topical action, the nail varnishes according to the invention in general comprise the antimycotic in an amount of 2 to 80, preferably 10 to 60, and in particular 20 to 40 wt. %.

The invention furthermore relates to the use of the nail varnish formulation according to the invention for the preparation of a medicament for treatment of growth disturbances of the nail.

EXAMPLE 1

A formulation according to the invention has the following composition:

| | |
|---|---|
| 6-Amino-4-piperidino-1,2-dihydro-1-hydroxy-2-iminopyrimidine | 2.5% |
| Ethyl acrylate/methyl methacrylate/trimethylammonioethyl methacrylate chloride in a molar ratio of 1:2:0,2 (c.f. Überzogene Arzneiformen [Coated drug forms], authors Bauer, Lehmann, Osterwald and Rothgang, pages 239–242, Wiss. Verlagsgesellschaft mbH, Stuttgart, 1988; EUDRAGIT ® RL 100) | 7.0.% |
| Ethanol 96% | 75.0% |
| Ethyl acetate | 10.5% |
| Butyl acetate | 5.0% |

The percentage amounts stated are based on the weight.

The nail varnish is prepared by dissolving the various components in the solvents.

The action of the formulations according to the invention is demonstrated in permeation tests on cow horn platelets and in treatment tests on subjects. The permeation test on cow horn platelets allows the release of an active compound from a specific formulation and the subsequent permeation through keratin material to be tested.

As a control example,

| | |
|---|---|
| 6-amino-4-piperidino-1,2-dihydro-1-hydroxy-2-iminopyrimidine | 2.5% |
| is dissolved in ethanol 96% | 97.5% |

A) Permeation Test on Cow Horn Platelets

The permeation of the active compound is measured by means of time-resolved Fourier transform infrared spectroscopy (c.f. Th. M. Bayerl et al.; J. Invest. Dermatol. 105:291–295, 1995) ATR technique:

100 µl of the test formulation (formulation according to the invention or control example) are applied to the upper side of a cow horn platelet 0.5 mm thick. The cow horn platelet is fixed with its underside to the upper side of a silicon crystal. After permeation of the active compound through the cow horn platelet, the FT-IR spectrum of the substance is influenced as a function of the concentration of active compound present, so that quantitative conclusions on the amount of active compound which has permeated as a function of time are possible by comparative measurements with the test formulation applied directly to the measurement crystal.

The experiments show that the nail varnish formulation according to the invention shows a permeation rate of the active compound through keratin material which is more than ten times that of the control example. This is a surprising finding since it could not have been foreseen that the active compound has a better bioavailability from the water-insoluble solid system present after the varnish formulation has dried than from the ethanolic solution.

B) Activity Test

The nail growth-promoting properties of the nail varnish formulation according to the invention was tested on 2 people. The untreated finger- and toenails of the other hand or the other foot in each case served as a direct comparison of growth. In order additionally to investigate or exclude a misinterpretation, specifically on the hands, because of a possibly faster growth of the nails on the working hand due to the better circulation of the nail organ which prevails there, the fingernails of the working hand of one test person and the fingernails of the non-working hand of the other test person are treated with the test formulation. The nails of the right working hand and the nails of the left foot are therefore treated with the test substance on one test person, while application of the formulation was the mirror image on the other test person.

To determine the growth rate, the length of all the nails is determined with a precision slide gauge, the proximal starting point of the measurement being the zenith of the lanula, since this point represents a fixed point. The edge of the nail is chosen as the distal limit.

Results: (increase in the growth in length of the treated against the untreated nail; treatment time 4 weeks once daily)

| Fingernails | |
| --- | --- |
| Treatment working hand | +45.3% |
| Treatment non-working hand | +18.6% |
| Toenails | |
| Treatment left foot | +27.6% |
| Treatment right foot | +23.9% |

In addition to the increase in growth in length, the increase in growth in area of the nails is determined by means of a transparent millimeter film.

Results: (Increase in the growth in area of the treated against the untreated nail; treatment time 4 weeks once daily)

| Fingernails | |
| --- | --- |
| Treatment working hand | +53.3% |
| Treatment non-working hand | +45.7% |
| Toenails | |
| Treatment left foot | +110.8% |
| Treatment right foot | +177.5% |

EXAMPLE 3

A formulation according to the invention has the following composition:

| | |
| --- | --- |
| 6-Amino-4-piperidino-1,2-dihydro-1-hydroxy-2-iminipyrimidine | 2.0% |
| 4-[3-[p-(1,1-dimethylpropyl)phenyl]-2-methyl-propyl]-2,6-dimethyl-morpholine hydrochloride | 5.0% |
| EUDRAGIT ® RL 100 | 10.0% |
| Ethanol 96% | 73.0% |
| Ethyl acetate | 10.0% |

EXAMPLE 4

A formulation according to the invention has the following composition:

| | |
| --- | --- |
| 4-Amino-4-piperidino-1,2-dihydro-1-hydroxy-2-iminopyrimidine | 2.5% |
| 1-Hydroxy-4-methyl-6-cyclohexyl-2-pyridone | 8.0% |
| 50% strength solution of a copolymer of methyl vinyl ether and maleic acid monobutyl ester in isopropanol | 35.0% |
| Ethanol 96% | 44.5% |
| Ethyl acetate | 10.0% |

EXAMPLE 5

A formulation according to the invention has the following composition:

| | |
| --- | --- |
| 5-[(3,4-Dimethyloxyphenethyl)methylamino]-2-(3,4-dimethyl-oxyphenyl)-2-isopropylvaleronitrile hydrochloride (verapamil hydrochloride) | 2.0% |
| 1-[2,4-Dichloro-β-2,4-dichlorobenzyloxy)phenethyl]imidazole (miconazole) | 2.0% |
| Polyvinylbutyral | 3.8% |
| Cellulose nitrate | 3.1% |
| Dibutyl phthalate | 0.6% |
| Ethyl acetate | 10.0% |
| Ethanol 96% | 78.5% |

EXAMPLE 6

A formulation according to the invention has the following composition:

| | |
| --- | --- |
| Angiotensin converting enzyme inhibitor in combination with the allyl antimycotic (2S,3aS,6aS)-1-[(S)-N-[(S)-1-ethoxycarbonyl-3-phenylpropyl]-alanyl]octahydrocyclopenta[b]pyrrole-2-carboxylic acid (ramipril) | 2.0% |
| (E)-N-(6,6-dimethyl-2-hepten-4-inyl)-N-methyl-1-nephthylmethylamine (terbinafin) | 0.5% |
| Methacrylic acid/ethyl acrylate 1:1 copolymer | 6.5% |
| Ethanol 96% | 71.0% |
| Ethyl acetate | 20.0% |

We claim:

1. A composition for application to a nail comprising a water-insoluble film-forming agent and a compound having a vasodilating action of the formula I:

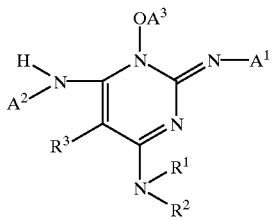

in which $R^1$ and $R^2$ independently of one another are
1) a hydrogen atom,
2) $(C_1-C_8)$-alkyl,
3) $(C_2-C_8)$-alkenyl,
4) phenyl-$(C_1-C_8)$-alkyl,
5) naphthyl-$(C_1-C_4)$-alkyl or
6) $(C_3-C_8)$-cycloalkyl, or
7) $R^1$ and $R^2$, together with the N atom, form a heterocyclic radical from the group consisting of
   7.1 aziridinyl,
   7.2 azetinyl,
   7.3 pyrrolidinyl,
   7.4 piperidinyl,
   7.5 hexahydroazepinyl,
   7.6 heptamethylimino,
   7.7 octamethylimino,
   7.8 morpholinyl or
   7.9 4-$(C_1-C_4)$-alkyl-piperazinyl, or
8) a radical from 7), in which the carbon atoms of the heterocyclic radicals are substituted by 1 to 3 $(C_1-C_4)$-alkyl radicals, $R^3$ is
1) a hydrogen atom,
2) $(C_1-C_8)$-alkyl,
3) $(C_2-C_8)$-alkenyl,
4) phenyl-$(C_1-C_8)$-alkyl,
5) naphtyl-$(C_1-C_8)$-alkyl,
6) benzyl,
7) phenyl,
8) naphthyl,
9) $(C_3-C_8)$-cycloalkyl or
10) $(C_1-C_6)$-alkyl, which is mono- or polysubstituted by halogen, and $A^1$, $A^2$ and $A^3$ independently of one another are a hydrogen atom or acetyl, or dihydralazine, diisopropylamine, diazoxide or nifedipine, nicardipine, diltiazem, nisoldipine, nitrendipine, nivaldipine, isradipine, felodipine, nimodipin, gallopamil, fendiline, flunarizine or amlodipine, diperdipine, fluspirilene, primozid, fantofaron, nicergoline, cyclandelate, or quinapril, lisinopril, benzazepril, captopril, ramipril, fosinopril, cifazapril, trandolapril, pentoxifylline, propentofylline, torbafylline, inner salt of 2,4-diamino-6-butoxy-3-sulfoxypyrimidine hydroxide, 2,6-diamino-4-piperidinopyridine, 2,6-diamino-4-butoxy-1,3,5-triazine 1-oxide or a mixture thereof.

2. A composition as claimed in claim 1, comprising a compound having a vasodilating action in an amount of from about 0.1 to about 10 percent by weight.

3. A composition as claimed in claim 1, further comprising an antimycotic having a topical action.

4. A composition as claimed in claim 3, comprising the antimycotic having a topical action in an amount of from about 0.5 to about 20 percent by weight.

5. A process for the preparation of a composition as claimed in claim 1, which comprises the step of mixing the water-insoluble film-forming agent, in dissolved form, with the compound having a vasodilating action.

6. A composition as claimed in claim 1, wherein the compound of Formula I is 6-amino-4-piperidino-1,2-dihydro-1-hydroxy-2-iminopyrimidine.

7. A composition as claimed in claim 1, wherein the film-forming agent is ethyl acrylate, said composition further comprising at least one polymer selected from a copolymer of ethyl acrylate/methyl methacrylate/trimethylammonloethyl methacrylate chloride, a copolymer of methyl vinyl ether and maleic acid monobutyl ester, a polymer of polyvinylbutyral and cellulose nitrate, and a copolymer of methacrylic acid.

8. A composition of claim 2, wherein the compound having a vasodilating action is in the amount of from about 2 to about 5 percent by weight.

9. A composition of claim 4, wherein the antimycotic is in the amount of from about 2 to about 5 percent by weight.

10. A process according to claim 9, further comprising the step of adding an antimycotic having topical action.

11. A process according to claim 5 or 10, further comprising the step of combining in further additives.

12. A process according to claim 11, wherein the additive is selected from a plasticizer, a colored pigment or dye stuff, a pearlescent agent, an agent which delays sedimentation, a sulfonamide resin, a silicate, an odiferous substance, a wetting agent, a lanolin derivative, a light protection agent, an antibacterial agent, a keratolytic agent, and a keratoplastic agent.

13. A method for the treatment of growth disturbances of a nail comprising the step of applying the composition of claim 1 to the surface of a nail in need of such treatment.

14. A method for stimulating nail growth comprising applying the composition of claim 1 to the surface of a nail.

15. A method comprising the step of applying the composition of claim 1 to the surface of a nail.

16. The composition as claimed in claim 3, wherein the antimycotic is selected from a hydroxypyridone, a morpholine derivative, an azole, and an allyl compound.

17. The composition as claimed in claim 16, wherein the hydroxypyridone is selected from ciclopirox, piroctone, and rilopirox.

18. A composition as claimed in claim 16, wherein the morpholine derivative is amorofine.

19. A composition as claimed in claim 16, wherein the azole is selected from bifonazole, clotrimazole, econazole, miconazole, oxiconazole, croconazole, fenticonazole, tioconazole, ketoconazole, and isoconazole.

20. A composition as claimed in claim 16, wherein the allyl compound is selected from terbinafin, naftifin, griseofulvin, tolciclate, tolnaftate, and butenafin.

* * * * *

UNITED STATES PATENT AND TRADEMARK OFFICE
CERTIFICATE OF CORRECTION

PATENT NO. : 6,007,798
DATED : December 28, 1999
INVENTOR(S) : Bohn et al

It is certified that error appears in the above-identified patent and that said Letters Patent is hereby corrected as shown below:

Claim 10, column 10, line 28, "claim 9" should read --claim 5--.

Signed and Sealed this

Twenty-eighth Day of November, 2000

Attest:

Q. TODD DICKINSON

*Attesting Officer*          *Director of Patents and Trademarks*